(12) United States Patent
Gage et al.

(10) Patent No.: US 11,065,377 B2
(45) Date of Patent: Jul. 20, 2021

(54) APPARATUS AND METHOD FOR CANNULATION OF VASCULAR ACCESS GRAFT

(71) Applicant: InnAVasc Medical, Inc., Durham, NC (US)

(72) Inventors: Shawn M. Gage, Raleigh, NC (US);
Jeffrey H. Lawson, Durham, NC (US);
Joseph Knight, Durham, NC (US);
Craig Nichols, Carrboro, NC (US)

(73) Assignee: InnAVasc Medical, Inc., Durham, NC (US)

( * ) Notice: Subject to any disclaimer, the term of this patent is extended or adjusted under 35 U.S.C. 154(b) by 0 days.

(21) Appl. No.: 15/941,599

(22) Filed: Mar. 30, 2018

(65) Prior Publication Data

US 2018/0289883 A1 Oct. 11, 2018

Related U.S. Application Data

(60) Provisional application No. 62/479,791, filed on Mar. 31, 2017.

(51) Int. Cl.
*A61M 1/36* (2006.01)
*A61M 39/02* (2006.01)
(Continued)

(52) U.S. Cl.
CPC ........... *A61M 1/3655* (2013.01); *A61B 17/11* (2013.01); *A61M 25/06* (2013.01);
(Continued)

(58) Field of Classification Search
CPC ...................... A61M 39/02–2039/0244; A61M 39/0247–2039/0291; A61M 5/42–427;
(Continued)

(56) References Cited

U.S. PATENT DOCUMENTS 1,017,301 A 2/1912 Lockwood
3,999,504 A 12/1976 Kearse
(Continued)

FOREIGN PATENT DOCUMENTS

AU 2011100534 A4 6/2011
AU 2012229032 B2 6/2015
(Continued)

OTHER PUBLICATIONS

INNAVASC Medical, Inc., International Patent Application No. PCT/US2018/025414, Invitation to Pay Additional Fees and Partial International Search Report, dated Jun. 27, 2018.
(Continued)

*Primary Examiner* — Manuel A Mendez
(74) *Attorney, Agent, or Firm* — Taylor English Duma LLC

(57) ABSTRACT

An apparatus for guiding cannulation with a dialysis needle of an arteriovenous dialysis access graft subcutaneously implanted in a body of a subject. The guiding apparatus comprises an elongated body member comprising a base portion terminating in longitudinal edges, a distance between the longitudinal edges of the base portion being substantially equal to a lateral dimension of the aces graft, and an elongated tubular sleeve defining an pocket having a longitudinal dimension and a lateral dimension configured to receive the body member. The body member is adapted to be received in the pocket of the sleeve for securing adjacent the subcutaneous access graft such that the inner surface of the base portion is aligned with a cannulation point of the graft for guiding location of a needle insertion.

10 Claims, 11 Drawing Sheets

(51) Int. Cl.
*A61B 17/11* (2006.01)
*A61M 25/06* (2006.01)

(52) U.S. Cl.
CPC .... *A61M 39/0208* (2013.01); *A61M 39/0247* (2013.01); *A61B 2017/1107* (2013.01); *A61M 2039/0223* (2013.01); *A61M 2039/0238* (2013.01); *A61M 2039/0258* (2013.01); *A61M 2039/0261* (2013.01); *A61M 2039/0264* (2013.01); *A61M 2039/0276* (2013.01); *A61M 2039/0279* (2013.01); *A61M 2039/0282* (2013.01); *A61M 2039/0288* (2013.01); *A61M 2039/0294* (2013.01); *A61M 2205/04* (2013.01); *A61M 2205/3515* (2013.01)

(58) Field of Classification Search
CPC .. A61M 2205/6045; A61M 2205/3515; A61M 1/3655
See application file for complete search history.

(56) References Cited

U.S. PATENT DOCUMENTS

| | | | |
|---|---|---|---|
| 4,004,298 A * | 1/1977 | Freed | A61M 39/0247 285/9.1 |
| 4,121,003 A | 10/1978 | Williams | |
| 4,228,796 A | 10/1980 | Gardiner | |
| 4,268,983 A | 5/1981 | Cook | |
| 4,723,544 A | 2/1988 | Moore et al. | |
| 4,733,661 A | 3/1988 | Palestrant | |
| 4,822,341 A | 4/1989 | Colone | |
| 5,123,907 A | 6/1992 | Romaine | |
| 5,147,307 A | 9/1992 | Gluck | |
| 5,167,629 A | 12/1992 | Vertenstein et al. | |
| 5,192,310 A | 3/1993 | Herweck et al. | |
| 5,312,350 A | 5/1994 | Jacobs | |
| 5,358,281 A | 10/1994 | Greig | |
| 5,364,361 A | 11/1994 | Battenfield | |
| 5,633,058 A | 5/1997 | Hoffer et al. | |
| 5,700,287 A | 12/1997 | Myers et al. | |
| 5,704,915 A | 1/1998 | Melsky et al. | |
| 5,713,859 A | 2/1998 | Finch et al. | |
| 5,849,036 A | 12/1998 | Zarate | |
| 6,024,723 A | 2/2000 | Cota | |
| 6,036,632 A | 3/2000 | Whitmore, III et al. | |
| 6,102,884 A | 8/2000 | Squitieri | |
| 6,146,414 A | 11/2000 | Gelman | |
| 6,261,257 B1 | 7/2001 | Uflacker et al. | |
| 6,283,942 B1 | 9/2001 | Staehlin et al. | |
| 6,428,504 B1 | 8/2002 | Riaziat et al. | |
| 6,500,109 B2 | 12/2002 | Tokita et al. | |
| 6,508,786 B2 | 1/2003 | Huitema et al. | |
| 6,547,820 B1 | 4/2003 | Staudenmeier | |
| 6,626,865 B1 | 9/2003 | Prisell | |
| 7,108,673 B1 | 9/2006 | Batiste | |
| 7,261,705 B2 | 8/2007 | Edoga et al. | |
| 7,452,374 B2 | 11/2008 | Hain et al. | |
| 7,527,593 B2 | 5/2009 | Fidel et al. | |
| 7,540,859 B2 | 6/2009 | Claude et al. | |
| 7,566,317 B1 | 7/2009 | Batiste et al. | |
| 7,670,333 B2 | 3/2010 | Schatzberger | |
| 7,713,234 B2 | 5/2010 | Karanzas | |
| 7,722,535 B2 | 5/2010 | Randlov et al. | |
| 7,740,593 B2 | 6/2010 | Shabaz | |
| 7,762,977 B2 | 7/2010 | Porter et al. | |
| 7,780,622 B2 | 8/2010 | Fitzpatrick et al. | |
| 7,780,662 B2 | 8/2010 | Bahney | |
| 7,806,922 B2 | 10/2010 | Henderson et al. | |
| 7,833,186 B1 | 11/2010 | Batiste | |
| 8,066,758 B2 | 11/2011 | Bogert et al. | |
| 8,075,525 B2 | 12/2011 | Yang | |
| 8,105,307 B2 | 1/2012 | Ponce | |
| 8,133,201 B1 | 3/2012 | Hurtado | |
| 8,152,751 B2 | 4/2012 | Roger et al. | |
| 8,162,884 B2 | 4/2012 | Van't Hooft | |
| 8,211,056 B2 | 7/2012 | Cull | |
| 8,414,530 B2 | 4/2013 | Mason | |
| 8,439,873 B1 | 5/2013 | Donovan | |
| 8,764,698 B2 | 7/2014 | Cull | |
| 8,784,359 B2 | 7/2014 | Plahey et al. | |
| 8,870,820 B2 | 10/2014 | Murphy et al. | |
| 8,882,694 B2 | 11/2014 | Li et al. | |
| 8,961,458 B2 | 2/2015 | Pesach et al. | |
| 8,992,453 B2 | 3/2015 | Vournakis et al. | |
| 9,023,051 B2 | 5/2015 | Hanson et al. | |
| 9,199,044 B2 | 12/2015 | Bangera et al. | |
| 9,585,998 B2 | 3/2017 | Gage et al. | |
| 9,694,145 B1 | 7/2017 | Onorato | |
| 9,700,674 B2 | 7/2017 | Despa et al. | |
| 9,757,515 B1 * | 9/2017 | Patel | A61M 5/162 |
| 2003/0100859 A1 | 5/2003 | Henderson et al. | |
| 2004/0153031 A1 | 8/2004 | Van Kaauwen | |
| 2004/0193106 A1 | 9/2004 | Miller | |
| 2004/0022044 A1 | 11/2004 | Hogendijk et al. | |
| 2005/0013850 A1 | 1/2005 | Caers et al. | |
| 2005/0148935 A1 | 7/2005 | Dimitrova et al. | |
| 2005/0267396 A1 | 12/2005 | Dame | |
| 2007/0123811 A1 | 5/2007 | Squitieri | |
| 2008/0146963 A1 | 6/2008 | Crocker et al. | |
| 2008/0195043 A1 | 8/2008 | Schwach et al. | |
| 2008/0221519 A1 | 9/2008 | Schwach et al. | |
| 2009/0209921 A1 | 8/2009 | Claude et al. | |
| 2010/0015590 A1 | 1/2010 | Kiss | |
| 2011/0060264 A1 | 3/2011 | Porter et al. | |
| 2011/0202003 A1 | 8/2011 | Cook | |
| 2011/0275930 A1 | 11/2011 | Cox et al. | |
| 2012/0245536 A1 * | 9/2012 | Gerber | A61M 39/0208 604/288.02 |
| 2012/0265138 A1 | 10/2012 | Harylka et al. | |
| 2013/0072883 A1 | 3/2013 | Edoga et al. | |
| 2013/0157924 A1 * | 6/2013 | Dewhurst | A61K 31/428 514/1.1 |
| 2013/0237929 A1 | 9/2013 | Hong et al. | |
| 2014/0018721 A1 | 1/2014 | Gage et al. | |
| 2014/0039453 A1 * | 2/2014 | Sonderegger | A61M 5/162 604/506 |
| 2014/0128842 A1 | 5/2014 | Deberadine | |
| 2014/0155819 A1 | 6/2014 | Amirouche et al. | |
| 2014/0200515 A1 | 7/2014 | Patterson et al. | |
| 2014/0257183 A1 | 9/2014 | Mica et al. | |
| 2014/0324021 A1 | 10/2014 | Ulrich et al. | |
| 2014/0336682 A1 | 11/2014 | Naoum | |
| 2015/0223906 A1 | 8/2015 | O'Neill et al. | |
| 2016/0136363 A1 | 5/2016 | McClellan | |
| 2016/0310663 A1 | 10/2016 | Dantsker | |
| 2016/0310679 A1 | 10/2016 | Hirth | |
| 2016/0354112 A1 | 12/2016 | Kustra et al. | |
| 2016/0375193 A1 | 12/2016 | Farzam et al. | |
| 2017/0173252 A1 | 6/2017 | Gage et al. | |
| 2017/0203053 A1 | 7/2017 | Burkett | |
| 2017/0340840 A1 | 11/2017 | Sweis | |
| 2018/0185059 A1 | 7/2018 | Rowe | |
| 2018/0193031 A1 | 7/2018 | Du et al. | |
| 2018/0280605 A1 | 10/2018 | Gage et al. | |
| 2018/0289901 A1 | 10/2018 | Boggild-Damkvist et al. | |
| 2020/0129749 A1 | 4/2020 | Gage | |
| 2020/0276430 A1 | 9/2020 | Gage et al. | |

FOREIGN PATENT DOCUMENTS

| | | |
|---|---|---|
| CN | 2693253 Y | 4/2005 |
| CN | 2855430 Y | 1/2007 |
| CN | 2875458 Y | 3/2007 |
| CN | 201211361 Y | 3/2009 |
| CN | 201596195 U | 10/2010 |
| CN | 201668815 U | 12/2010 |
| CN | 201996908 U | 10/2011 |
| CN | 202223661 U | 5/2012 |
| CN | 102580192 A | 7/2012 |
| CN | 102580193 A | 7/2012 |
| CN | 102580194 A | 7/2012 |
| CN | 102580195 A | 7/2012 |
| CN | 102580196 A | 7/2012 |
| CN | 102600532 A | 7/2012 |

(56) References Cited

FOREIGN PATENT DOCUMENTS

| | | |
|---|---|---|
| CN | 102600533 A | 7/2012 |
| CN | 102600534 A | 7/2012 |
| CN | 102631734 A | 8/2012 |
| CN | 103495244 A | 1/2014 |
| CN | 203389172 U | 1/2014 |
| CN | 203885933 U | 10/2014 |
| CN | 204181970 U | 3/2015 |
| CN | 204446835 U | 7/2015 |
| CN | 204619059 U | 9/2015 |
| CN | 204635146 | 9/2015 |
| CN | 204655694 U | 9/2015 |
| CN | 204655695 U | 9/2015 |
| CN | 204655696 U | 9/2015 |
| CN | 204745226 U | 11/2015 |
| CN | 105268063 A | 1/2016 |
| CN | 205031669 U | 2/2016 |
| CN | 205360154 U | 7/2016 |
| CN | 205515823 U | 8/2016 |
| CN | 205698760 U | 11/2016 |
| CN | 206183758 U | 5/2017 |
| CN | 107865990 A | 4/2018 |
| CN | 108114350 A | 6/2018 |
| CN | 108283756 A | 7/2018 |
| CN | 108525077 A | 9/2018 |
| DE | 102004037207 A1 | 4/2005 |
| EP | 1426067 A1 | 6/2004 |
| EP | 2686033 B1 | 5/2015 |
| FR | 2980977 | 4/2013 |
| GB | 2202445 | 9/1988 |
| KR | 101732305 | 5/2017 |
| WO | 8000060 | 1/1980 |
| WO | 2005002661 A1 | 1/2005 |
| WO | 2011112755 | 9/2011 |
| WO | 2011112755 A2 | 9/2011 |
| WO | 12006790 A1 | 1/2012 |
| WO | 2012125927 A2 | 9/2012 |
| WO | 13061352 A1 | 5/2013 |
| WO | 2016179457 A1 | 11/2016 |
| WO | 18191121 A1 | 10/2018 |
| WO | 2018183854 A1 | 10/2018 |
| WO | 2018183886 A1 | 10/2018 |
| WO | 2020092441 | 5/2020 |

OTHER PUBLICATIONS

INNAVASC Medical, Inc., International Patent Application No. PCT/US2018/025414, International Search Report and Written Opinion, dated Aug. 21, 2018.

Gage, Shawn M.; Non-Final Office Action for U.S. Appl. No. 14/027,986, filed Sep. 16, 2013, dated Apr. 1, 2016, 13 pgs.

Gage, Shawn M.; Restriction Requirement for U.S. Appl. No. 14/027,986, filed Sep. 16, 2013, dated Jan. 13, 2016, 9 pgs.

Gage, Shawn M.; Issue Notification for U.S. Appl. No. 14/027,986, filed Sep. 16, 2013, dated Feb. 15, 2017, 1 pg.

Gage, Shawn M.; Notice of Allowance for U.S. Appl. No. 14/027,986, filed Sep. 16, 2013, dated Nov. 2, 2016, 7 pgs.

Gage, Shawn M.; Non-Final Office Action for U.S. Appl. No. 15/450,523, filed Mar. 6, 2017, dated Jan. 23, 2019, 9 pgs.

Gage, Shawn M.; Requirement for Restriction/Election for U.S. Appl. No. 15/450,523, filed Mar. 6, 2017, dated Jul. 12, 2018, 9 pgs.

Gage, Shawn, Notice of Allowance for U.S. Appl. No. 15/450,523, filed Mar. 6, 2017, dated May 17, 2019, 7 pages.

Gage, Shawn M; International Preliminary Report on Patentaiblity for serial No. PCT/US2012/029449, filed Mar. 16, 2012, dated Sep. 26, 2013, 6 pgs.

Gage, Shawn M; International Search Report and Written Opinion for serial No. PCT/US2012/029449, filed Mar. 16, 2012, dated Oct. 29, 2012, 8 pgs.

Gage, Shawn M.; Office Action for Australian serial No. 2012229032, filed Mar. 16, 2012, dated Feb. 9, 2015, 3 pgs.

Gage, Shawn M.; Office Action for Canadian serial No. 2,829,766, filed Mar. 16, 2012, dated Jan. 10, 2018, 5 pgs.

Gage, Shawn M.; Extended European Search Report for serial No. 12757046.3, filed Mar. 16, 2012, dated Jan. 3, 2014, 7 pgs.

Gage, Shawn M.; Decision to Grant for European serial No. 12757046.3, filed Mar. 16, 2012, dated Apr. 10, 2015,2 pgs.

Gage, Shawn M.; Intention to Grant for European serial No. 12757046.3, filed Mar. 16, 2012, dated Nov. 19, 2014,8 pgs.

Gage, Shawn M.; International Search Report and Written Opinion for serial No. PCT/US2018/025456, filed Mar. 30, 2018, dated Jun. 25, 2018, 12 pgs.

Gage, Shawn M.; Non-Final Office Action for U.S. Appl. No. 15/941,790, filed Mar. 30, 2018; dated Jul. 20, 2020; 50 pages.

Gage, Shawn M.; Final Office Action dated Jun. 27, 2019, for U.S. Appl. No. 16/175,698, filed Oct. 30, 2018, 18 pages.

Gage, Shawn M.; Non-Final Office Action issued for U.S. Appl. No. 16/175,698, filed Oct. 30, 2018; dated Mar. 31, 2020; 41 pages.

Gage, Shawn; Applicant Initiated Interview Summary for U.S. Appl. No. 16/175,698, filed Oct. 30, 2018; dated Oct. 24, 2019; 6 pages.

Gage, Shawn; International Preliminary Report on Patentability for PCT Application No. PCT/US2018/025414, filed Mar. 30, 2018; dated Oct. 10, 2019; 14 pages.

Gage, Shawn; International Preliminary Report on Patentability for PCT Application No. PCT/US2018/025456, filed Mar. 30, 2018; dated Oct. 10, 2019; 9 pages.

Gage, Shawn M.; International Search Report and Written Opinion for PCT Application No. PCT/US2019/058665, filed Oct. 29, 2019; dated Apr. 2, 2020; 16 pages.

Gage, Shawn M.; Final Office Action for U.S. Appl. No. 16/175,698, filed Oct. 30, 2018, dated Jan. 22, 2021, 24 pages.

* cited by examiner

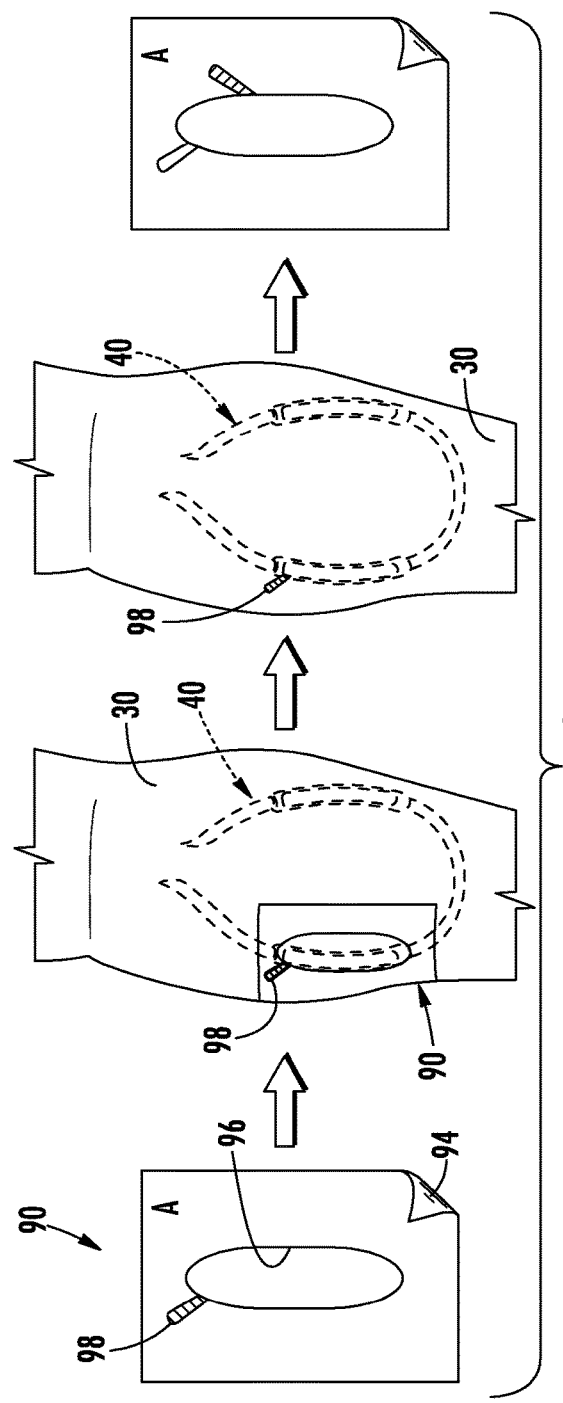
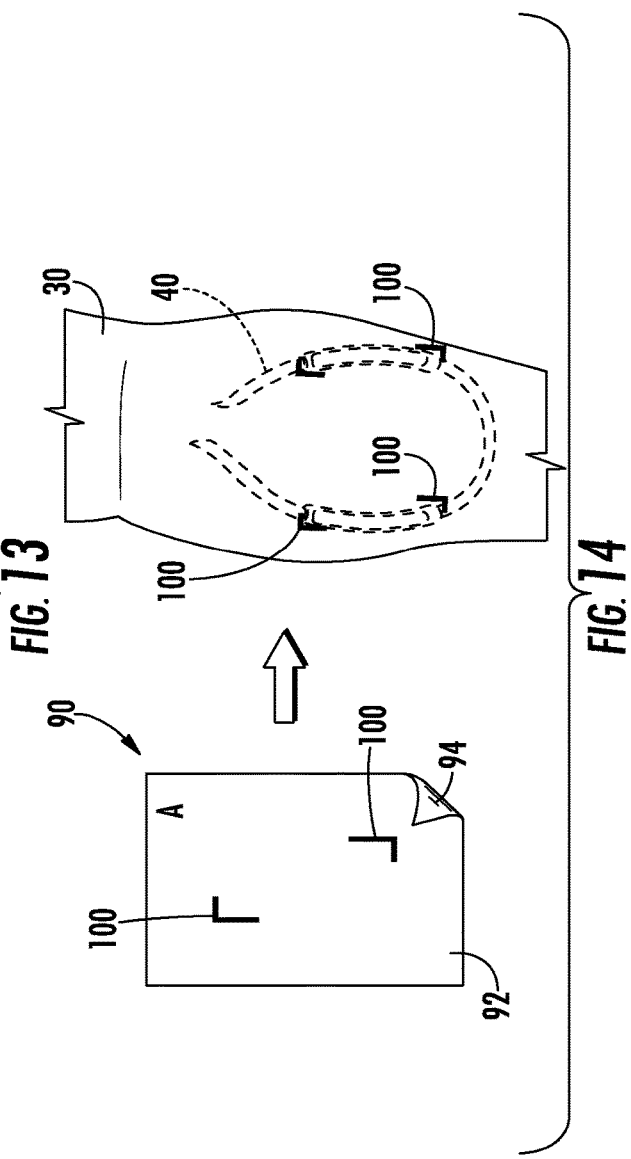
FIG. 13
FIG. 14

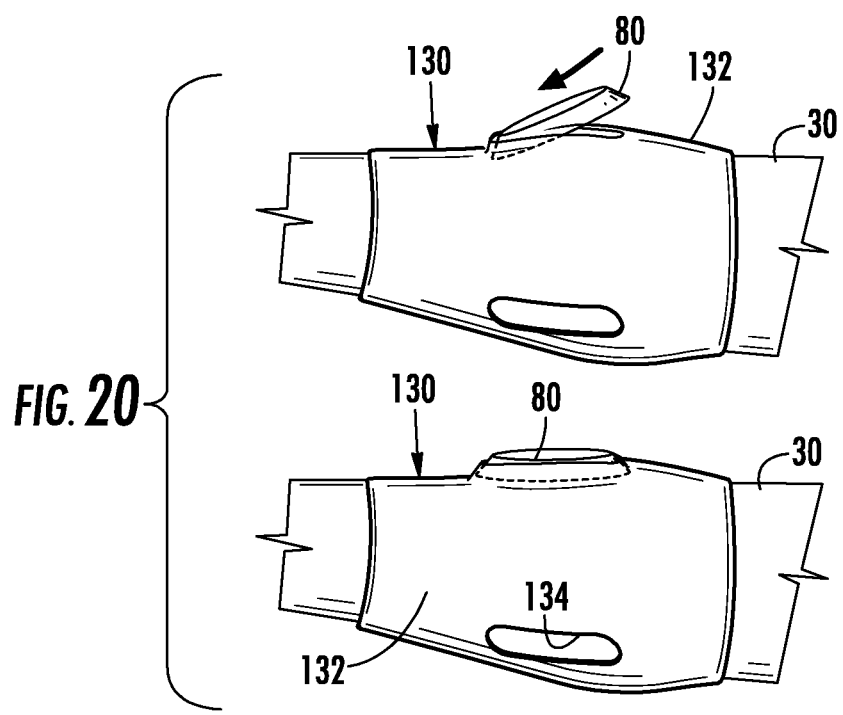

1

APPARATUS AND METHOD FOR CANNULATION OF VASCULAR ACCESS GRAFT

CROSS-REFERENCES

This application is related to U.S. provisional application No. 62/479,791, filed Mar. 31, 2017, entitled "APPARATUS AND METHOD FOR CANNULATION OF VASCULAR ACCESS GRAFT", naming Shawn M. Gage and Jeffrey H. Lawson as the inventors. The contents of the provisional application are incorporated herein by reference in their entirety, and the benefit of the filing date of the provisional application is hereby claimed for all purposes that are legally served by such claim for the benefit of the filing date.

BACKGROUND

An apparatus and method is described for needle access of a surgically created vascular access for use as a means to receive hemodialysis and other procedures requiring vascular access and, more particularly, an apparatus and method for vascular access of an arteriovenous graft or arteriovenous fistula that enables location of cannulation sites post-implant.

Hemodialysis is a life-sustaining treatment for patients with end stage renal disease. Hemodialysis is a process whereby large amounts of blood are removed from the body, filtered through a machine that removes wastes, and then returned into the body.

A vascular access site on the body where blood will be removed and returned during dialysis is prepared before starting hemodialysis. Creation of an arteriovenous fistula ("AVF") is achieved in a surgical procedure in which a vein is connected directly to an artery. The connection between the artery and the vein may be formed using an arteriovenous graft ("AVG") made from a synthetic material and implanted just under the skin. Placement sites for AVG's include, without limitation, the forearm, upper arm, neck, chest, and thigh, in either straight or looped configurations. Once surgically positioned, an AVG becomes a conduit that can be used repeatedly for blood access during hemodialysis. Needles are used to cannulate the graft through the skin, directly puncturing the walls of the graft. In conventional hemodialysis, two cannulas are placed in the access graft, with one needle puncture being made in the graft wall in the arterial side and another needle puncture being made in the venous side. During dialysis, blood is withdrawn from the arterial side of the graft, passed through a hemodialysis machine, and then returned to the patient through the second needle inserted in the venous side of the graft.

A significant step in the hemodialysis procedure is "finding" the proper position within the graft to perform the needle sticks. Moreover, conventional dialysis protocols require a patient to undergo a dialysis procedure at least three times a week. As a result, the skin and underlying tissue are punctured numerous times per week to gain entry into the implanted AVG. The technique of cannulating an AVF or AVG for hemodialysis requires considerable skill. A vascular access often lies several centimeters below the surface of the skin and cannot be located by visual inspection. A medical technician is required to locate the AVF or AVG by palpation, which can prove to be extremely difficult. The punctures of the vascular access are prone to error and complication. Punctures done incorrectly may promote rupture of the access, bleeding, hematoma formation, pseudoaneurysm formation, severe pain or the development of organized thrombi within the lumen of the graft. The formation of such blood clots may result not only in multiple graft thromboses, but may eventually lead to graft failure. Missing the vascular access entirely or improperly positioning of the needle within the lumen of the AVF or AVG device are two contraindications, which adversely affect the time the graft remains patent. Locating the cannulation area simply by using conventional methods of palpating through the skin is sometimes unreliable.

For the forgoing reasons, there is a need for an apparatus and method for proper cannulation of a vascular access graft or fistula, including correct identification of an access region of the vascular access following implantation. The new apparatus should improve access to the implanted AVF or AVG device by allowing a user of the vascular access to facilitate accurate and reproducible entry into the implanted AVF or AVG of dialysis needles, cannulas, and the like, which are introduced into the vascular access via insertion through the skin.

SUMMARY

An apparatus is provided for guiding cannulation with a dialysis needle of an arteriovenous dialysis access graft subcutaneously implanted in a body of a subject. The arteriovenous dialysis graft includes a flexible conduit defining a longitudinal flow passageway and has a first end portion configured to connect to an artery of the subject and a second end portion configured to connect to a vein of the subject such that blood flows through the longitudinal flow passageway of the conduit from the first end portion to the second end portion. A cannulation chamber defines a cannulation port, the conduit extending through the cannulation chamber for receiving the needle inserted through the cannulation port. The guiding apparatus comprises an elongated body member having a longitudinal axis and an inner surface. The body member comprises a base portion terminating in longitudinal edges. A distance between the longitudinal edges of the base portion is substantially equal to a lateral dimension of the cannulation chamber. Legs extend from the longitudinal edges of the base portion, the legs terminating in longitudinal edges. The base portion and legs define an open longitudinal channel for receiving the cannulation chamber. The body member is adapted to be secured adjacent the subcutaneous cannulation chamber such that the legs operatively engage the cannulation chamber for aligning the inner surface of the base portion with the cannulation port for guiding location of a needle insertion through the body member and into the cannulation chamber.

In one aspect, the body member has a first end and a second end, and wherein the body member is adapted to extend from the first end to the second end of the cannulation chamber. The body member may have at least one passage opening into the inner surface of the body member for passing a needle.

In another aspect, at least a portion of the cannulation chamber and the body member comprise a substantially magnetic or paramagnetic material.

In another embodiment, an apparatus is provided for guiding cannulation with a dialysis needle of an arteriovenous dialysis access graft subcutaneously implanted in a body of a subject. The arteriovenous dialysis graft includes a flexible conduit defining a longitudinal flow passageway and having a first end portion configured to connect to an artery of the subject and a second end portion configured to connect to a vein of the subject such that blood flows through the longitudinal flow passageway of the conduit from the first end portion to the second end portion. A cannulation chamber defines a cannulation port between the first end portion and the second end portion, the conduit extending through the cannulation chamber for receiving the needle inserted through the cannulation port. The guiding apparatus comprises an elongated tubular sleeve having a longitudinal axis. The sleeve defines an opening having a longitudinal dimension and a lateral dimension adapted to be substantially equal to a longitudinal dimension and a lateral dimension of the cannulation chamber. The sleeve is configured to accommodate the body of the subject adjacent the subcutaneous cannulation chamber of the access graft such that the opening surrounds the cannulation chamber for guiding location of a needle insertion into the cannulation port.

In one aspect, the material of the sleeve is selected from a film, paper, a woven fabric, or a non-woven fabric.

In still another embodiment, an apparatus is provided for guiding cannulation with a dialysis needle of an arteriovenous dialysis access graft subcutaneously implanted in a body of a subject. The arteriovenous dialysis graft includes a flexible conduit defining a longitudinal flow passageway and having a first end portion configured to connect to an artery of the subject and a second end portion configured to connect to a vein of the subject such that blood flows through the longitudinal flow passageway of the conduit from the first end portion to the second end portion. A cannulation chamber defines a cannulation port between the first end portion and the second end portion. The conduit extends through the cannulation chamber for receiving the needle inserted through the cannulation port. The guiding apparatus comprises an elongated body member having a longitudinal axis and an inner surface. The body member comprises a base portion terminating in longitudinal edges, a distance between the longitudinal edges of the base portion being substantially equal to a lateral dimension of the cannulation chamber. An elongated tubular sleeve has a longitudinal axis, the sleeve defining a pocket having a longitudinal dimension and a lateral dimension configured to receive the body member. The body member is adapted to be received in the pocket of the sleeve for securing adjacent the subcutaneous cannulation chamber such that the inner surface of the base portion is aligned with the cannulation port for guiding location of a needle insertion through the body member and into the cannulation chamber.

A kit is also provided and comprises at least one dialysis needle for accessing an arteriovenous dialysis access graft subcutaneously implanted in a body of a subject. The arteriovenous dialysis graft includes a flexible conduit defining a longitudinal flow passageway and having a first end portion configured to connect to an artery of the subject and a second end portion configured to connect to a vein of the subject such that blood flows through the longitudinal flow passageway of the conduit from the first end portion to the second end portion. A cannulation chamber defines a cannulation port, the conduit extending through the cannulation chamber for receiving the needle inserted through the cannulation port. A dispenser is provided for accommodating a plurality of elongated body members, each body member having a longitudinal axis and an inner surface. The body member comprises a base portion terminating in longitudinal edges, a distance between the longitudinal edges of the base portion being substantially equal to a lateral dimension of the cannulation chamber. The body member is adapted to be secured adjacent the subcutaneous cannulation chamber such that the legs operatively engage the cannulation chamber for aligning the inner surface of the base portion with the cannulation port for guiding location of a needle insertion. Each body member has at least one passage opening into the inner surface of the body member for passing a needle, the needle passage of the body member being in a different position than the needle passage of any other body member.

BRIEF DESCRIPTION OF THE DRAWINGS

For a more complete understanding of the present invention, reference should now be had to the embodiments shown in the accompanying drawings and described below. In the drawings:

FIG. 13 is top plan views of an embodiment of a frangible adhesive applicator device for guiding cannulation of a subcutaneous arteriovenous graft including each of a pair of cannulation chambers shown in phantom.

FIG. 14 is top plan views of another embodiment of a frangible adhesive applicator device for guiding cannulation of a subcutaneous arteriovenous graft including each of a pair of cannulation chambers shown in phantom.

FIG. 20 is perspective views of the sleeve as shown in FIG. 18 including the applicator device.

DESCRIPTION

As used herein, the term "vascular access" is used to mean an intended surgical connection between the arterial and venous system through which blood flows from the artery to the vein. As noted above, this can be achieved by directly connecting a vein to an artery (AVF) or by utilizing a synthetic or autologous conduit to connect the arterial and venous systems (AVG). Because there are many types of AVG's and associated components that are well known in the art and that may be utilized to practice the present invention, a more detailed description of these components is not required. It is understood that the present invention is not directed to any particular type of AVG. The vascular access graft apparatus and method described herein is for use in medical procedures requiring vascular access. Accordingly, the features described herein may be used with any conventional vascular access graft including AVG's including, but not limited to, the AVG described by U.S. Pat. No. 9,585,998, the contents of which are hereby incorporated by reference herein in their entirety. A similar application is shown and described in U.S. Pub. Application No. 2014/0336682, the contents of which are also incorporated by reference herein in their entirety. Accordingly, detailed explanations of the functioning of all of the components and use of the grafts are deemed unnecessary for understanding of the present description by one of ordinary skill in the art.

Certain terminology is used herein for convenience only and is not to be taken as a limiting. For example, words such as "upper," "lower," "left," "right," "horizontal," "vertical," "upward," "downward," "top" and "bottom" merely describe the configurations shown in the FIGS. Indeed, the components may be oriented in any direction and the terminology, therefore, should be understood as encompassing such variations unless specified otherwise. The words "interior" and "exterior" refer to directions toward and away from, respectively, the geometric center of the core and designated parts thereof. The terminology includes the words specifically mentioned above, derivatives thereof and words of similar import.

Figure 1:
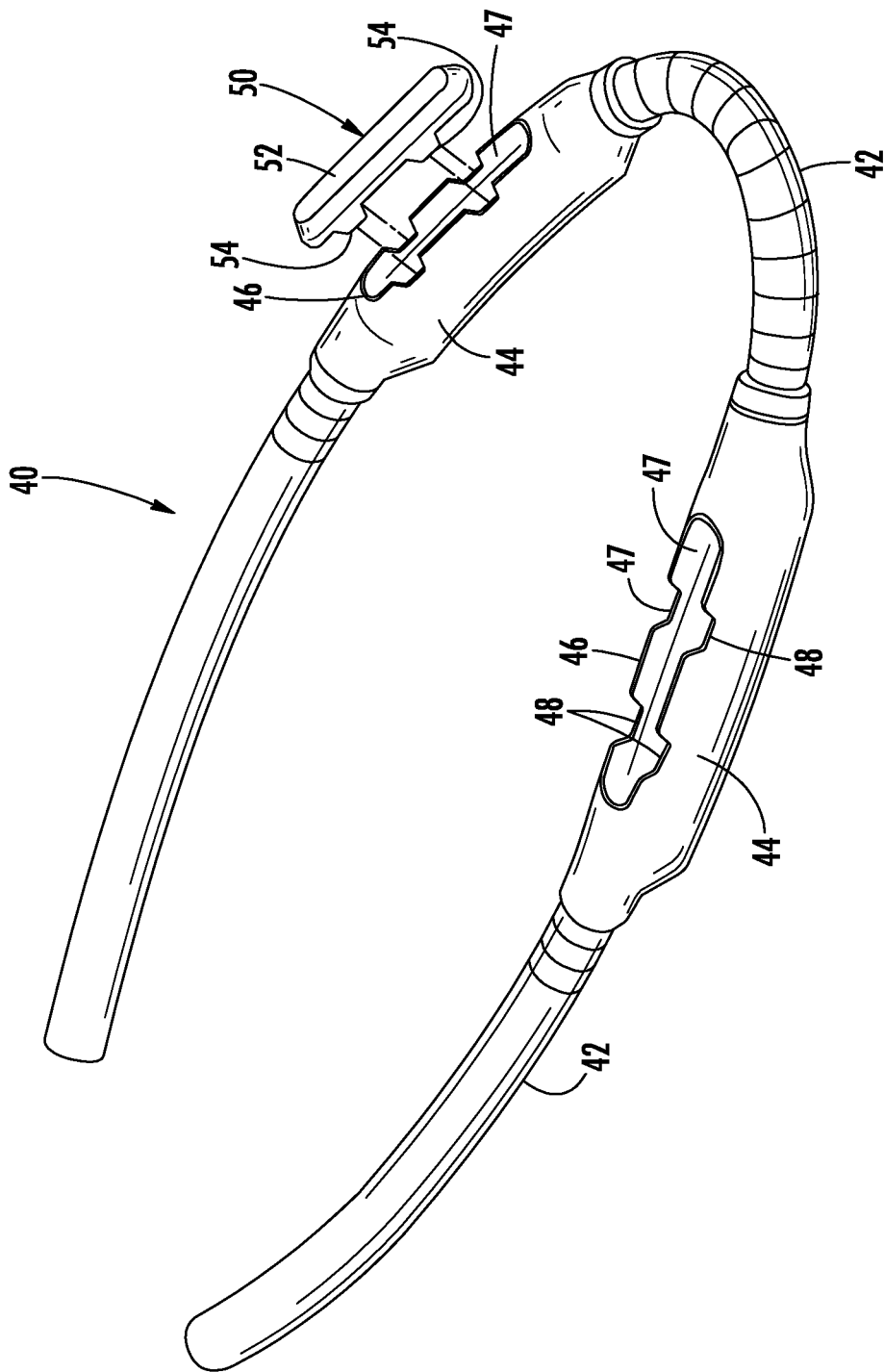
FIG. 1 is an exploded perspective view an embodiment of an applicator device for cannulation of an arteriovenous graft including a cannulation chamber.

Referring now to the drawings, wherein like reference numerals designate corresponding or similar elements throughout the several views, a vascular access graft for connecting an artery to a vein is shown in FIG. 1 and generally designated at 40. The vascular access graft 40 includes a tubular portion 42 of biocompatible material for conducting fluid such as blood. As is conventional, the tubular portion 42 is anastomosed at a first end to an artery and anastomosed to a vein at a second end (not shown). A pair of spaced cannulation chambers 44 are disposed intermediate along the length of the tubular portion in fluid communication with the arterial side and the venous side of the vascular access graft 40.

An applicator device for use in identifying a needle insertion location for cannulation of an implanted vascular access graft 40 is also shown in FIG. 1 and generally designated at 50. The applicator device 50 is adaptable to the cannulation chamber 44 of the vascular access graft 40 allowing for a highly localized, accurate delivery of a needle into a predetermined portion of the cannulation chamber 44. The term "adaptable" as used herein includes any corresponding fixing or aligning means for positioning the applicator device 50 relative to the cannulation chamber 44. Thus, it is understood that multiple means of adaptation are anticipated that can be used to align the applicator device to a wide range of vascular access grafts.

The applicator device can be formed of either synthetic or natural materials, including, but not limited to, thermoplastics, thermoset polymers, elastomers, rubbers, or woven or non-woven composite materials. The applicator device may be, for example, any suitable molded form of a polymeric, plastic foam (including open celled foam), woven composite or non-woven composite, mixtures thereof, or the like. In particular, a suitable applicator device may thus be prepared, for example, from Nylon, a polyolefin, such as polyethylene, including UHMW polyethylene, structural plastics such as PEEK (polyetheretherketone), polysulfone, polypropylene, ethylene propylene copolymers, and ethylene butylene copolymers, polyurethanes, polyurethane foams, polystyrenes, plasticized polyvinylchlorides, polyesters, Delrin polyacetal, and polyamides, and homopolymer and copolymers of the above. The applicator device can also be made of a gel-like substance to provide pressure for hemostasis when compressed. The applicator may be doped with one or more drugs to aid in the process of cannulation and/or removing needles. For example, Lidocaine may be added to help minimize pain of a needle stick, and/or a topical hemostatic may be incorporated to aid in the cessation of bleeding. Many combinations of drug combinations with the applicator may be expected. It is understood that the applicator device may assume a variety of shapes as necessary to accommodate and adapt to a variety of vascular access grafts and cannulation chambers. It is further understood that a needle passage may be provided where the material of the applicator device is too hard to allow penetration by the needle.

Figure 2:
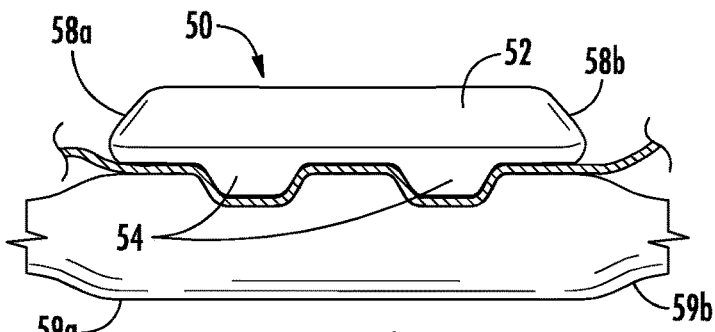
FIG. 2 is a longitudinal cross-section view of the applicator device as shown in FIG. 1 in position on a subcutaneous cannulation chamber.
Figure 3:
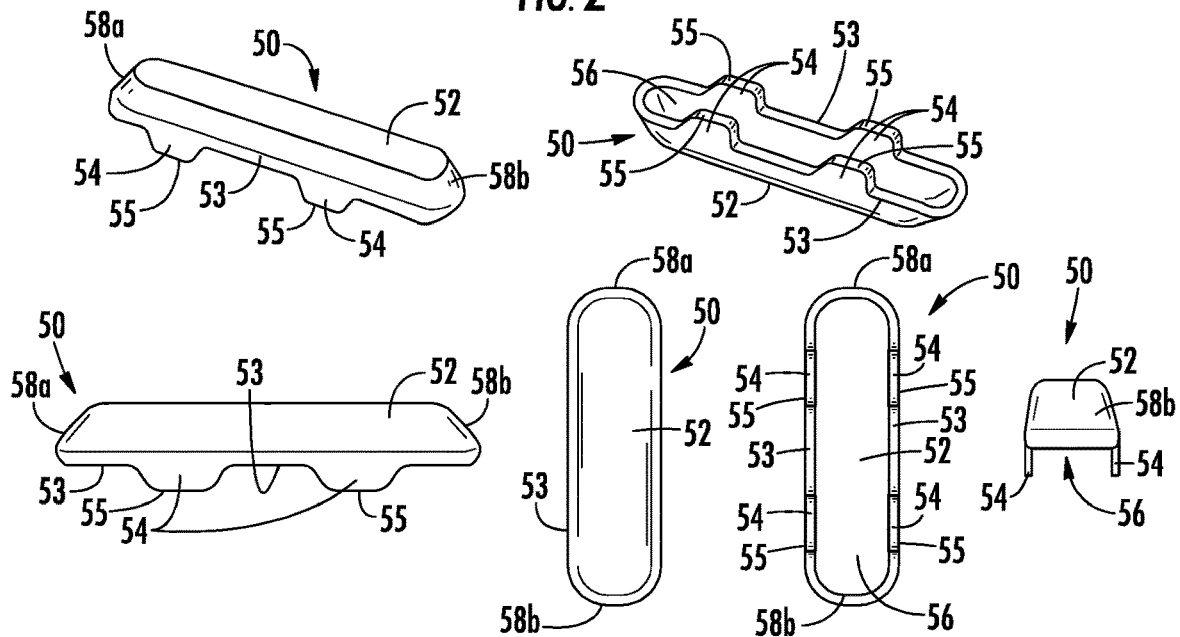
FIG. 3 is top and bottom perspective views, side and end elevation views, and top and bottom plan views of the applicator device as shown in FIG. 1.

In one aspect, the applicator device 50 may be configured to be adaptable to an implanted vascular access graft 40 by fitting onto the implanted graft in the manner of a puzzle piece. In this embodiment, the "fit-on" applicator device 50 as shown in FIG. 3 is an elongated member having a substantially oval profile and comprising a substantially major base portion 52 having a longitudinal axis. The base portion 52 spans between generally planar side walls 54, or legs, two of which depend from the longitudinal edges 53 of each side of the base portion 52. The legs 54 depend generally perpendicularly along a length of the edges 53 of the base portion 52. Each of the legs 54 terminates in longitudinal edges 55. The base portion 52 and the legs 54 define an open longitudinal channel 56. Referring to FIGS. 1 and 2, the applicator device 50 having this configuration is adaptable to an AVG 40 including a cannulation chamber 44 having an upper peripheral rim 46 defining spaced notches 48 for receiving the legs 54 of the applicator device 50. In use, the applicator device 50 is adapted to the AVG 40 by positioning the device over the cannulation chamber 44 such that the legs 54 fit into the notches 48 with the skin captured between. In this arrangement, the applicator device 50 indicates the position of the cannulation chamber 44 and the user may then select a desired location along the length of the cannulation chamber for needle insertion.

Referring to FIG. 2, in use, the vascular access graft 40 is implanted under the skin of the patient with one end 59a grafted into an artery and the other end 59b grafted into a vein whereby fluidic continuity is established from the artery through the lumen of the tubular element and into the vein. In a method of performing hemodialysis on a patient using the vascular access graft 40, the lumen of the vascular access graft 40 is connected via a needle to a hemodialysis filtration unit such that blood can be diverted from the lumen into the hemodialysis filtration unit, filtered, and then returned into the lumen. It is understood that the vascular access graft 40 may have uses other than for dialysis. Such uses include situations where patients require frequent vascular injections or infusions of therapeutic fluids. In all cases, use of the applicator devices, stickers, straps and sleeves typically greatly reduces the number of "missed" needle sticks, and generally facilitates greater accuracy in identifying the implanted device into which needle cannulation is desired.

The applicator device 50 is manually aligned with the cannulation chamber 44 such that the legs 54 correspond to the notches 48 in the cannulation chamber 44. The applicator device 50 is then pressed in a direction toward the cannulation chamber 44 such that the legs 54 engage in the notches 48. During downward movement of the device 50 the legs 54 are slidably received in the longitudinal notches 48 in the peripheral rim 46 of the cannulation chamber 44. The applicator device 50 is thus aligned in a positioned so that the device is located over the cannulation chamber 44 as shown in FIG. 1. The user then inserts one or more needles into the cannulation chamber 44 to commence hemodialysis. Needle insertion is facilitated such the user may do so as quickly and accurately as possible with minimal blood loss and maximum benefit to the user.

Figure 4:
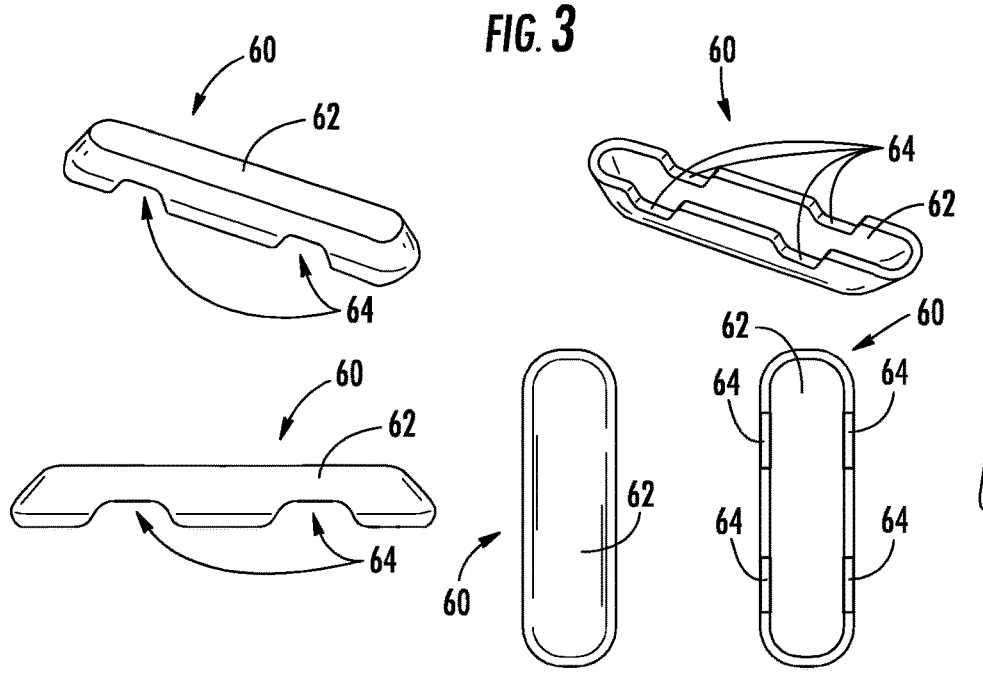
FIG. 4 is top and bottom perspective views, side and end elevation views, and top and bottom plan views of a second embodiment of an applicator device for cannulation of an arteriovenous graft including a cannulation chamber as shown in FIG. 1.

Another embodiment of a "fit-on" applicator device is shown in FIG. 4 and generally designated at 60. As in the previous embodiment, the applicator device 60 is an elongated member having a substantially oval profile and comprises a substantially major base portion 62 having a longitudinal axis. In this embodiment, the base portion 62 defines spaced notches 64 formed along the longitudinal edges of each side of the base portion 62. The applicator device 60 having this configuration is adaptable to an AVG 40 including a cannulation chamber 44 having legs (not shown) projecting outwardly from an upper peripheral rim 46 for insertion into the spaced notches 64 of the applicator device 60. In use, the applicator device 60 is adapted to the AVG 40 by positioning the device over the cannulation chamber 44 such that the legs fit into the notches 64. In this arrangement, the applicator device 60 indicates the position of the cannulation chamber 44 and the user may then select a desired location along the length of the device for insertion of a needle.

Figure 5A:
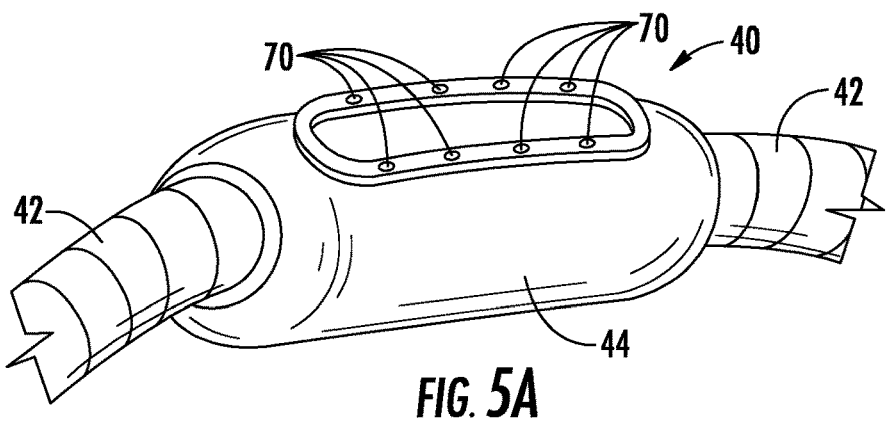
FIG. 5A is a perspective view of an embodiment of a portion an arteriovenous graft including a cannulation chamber.

In another embodiment, the vascular access graft 40 comprises one or more fixably-positioned magnetic, paramagnetic or ferromagnetic materials 70 creating one or more distinct sites on the cannulation chamber 44 as shown in FIG. 5A. In the embodiment shown, the magnetic or paramagnetic sites are disposed circumferentially along the peripheral rim 46 on the upper surface of the cannulation chamber 44. This arrangement substantially defines the border of a port 47 of the cannulation chamber 44 configured for receiving needle punctures. Following implantation, the cannulation chamber 44 may be located within the patient's body by passing a magnet over the surface of the patient's skin in proximity to the implantation site, thereby allowing the magnets 70 to essentially identify the optimal site for needle access or puncture of the vascular access graft during cannulation.

A locator or detector (not shown), including one or more magnets, may be used for locating the implanted graft and identifying the cannulation chamber 44 for needle insertion and access. The locator, or "wand", is passed over the skin in suspected proximity to the implanted graft. The wand is used then to identify and to locate the cannulation chamber 44, or one or more sites in, on, or about the implanted graft where cannulation should optimally occur. This "localizing" ability of a magnet-containing detector can make it easier to find the proper cannulation site while minimizing damage to the vascular access graft. The cannulation chamber 44 is localizable through the skin with a high degree of accuracy and precision by passing the wand over the surface of the skin in the region proximate to the implant. This allows the user to perform needle insertion, or cannulation, to at least one or more selected locations in the port 47 region as defined by the presence of the one or more magnetic material sites. It is possible to extend this to applications for detecting the implanted AVG via an RFID tag, a concentration of specific material that would be detected by Near Infrared light/visible light spectroscopy, or other methods known in the art.

While any suitably sized magnets may be used, exemplary magnets include Neodymium Iron Boron (NdFeB) cylindrically shaped (e.g., "button") magnets. In certain embodiments, the magnets may be coated with one or more protective layers to facilitate maximum protection and durability. Preferably, the paramagnetic material used in formation of the disclosed medical devices will include, consist essentially of, or consist of, iron, steel, cobalt, nickel, a ceramic material, surgical-grade steel, or an alloy or combination thereof. Alternatively, the material used in the formation of the disclosed medical devices may include, consist essentially of, or consist of, a superparamagnetic material, including for example, superparamagnetic metal oxide nanoparticles (e.g., superparamagnetic iron oxide nanoparticles [SPIOs] [see e.g., Ji et al. (2007)].

The number of magnet sites 70 spaced around the rim 46 of the cannulation chamber 44 may be of any practical number. It is envisioned that the vascular access graft comprises from 2 to about 8 or 10 magnetic sites placed equidistant along a substantial portion of the long axis of the graft 10. Exemplary magnets for use with the disclosed access devices, grafts, and vascular access ports will preferably include, consist essentially of, or alternatively consist of, a ceramic, lanthanoid, paramagnetic, ferrimagnetic, or ferromagnetic material, including, but not limited to, those that include aluminum, boron, cobalt, copper, iron, neodymium, nickel, samarium, titanium, or a combination or alloy thereof, including, but not limited to commercially-available permanent alloy magnets, such as, without limitation, NdFeB, AlNi, AlCoMax, AlNiCo, TiConAl, and the like.

In use, the user places the detector "wand" over the skin above the implanted vascular access graft 40. The magnets on the wand detect the magnetic sites of the surface of the cannulation chamber 44 of the implanted vascular access graft and localize it. A needle is inserted through the skin into the port 47 of the cannulation chamber 44 as identified by the wand. Localization and identification of the vascular access graft 40 following implantation is facilitated by the presence of the one or more magnetic material sites 70 included with the cannulation chamber 44.

Figure 5B:
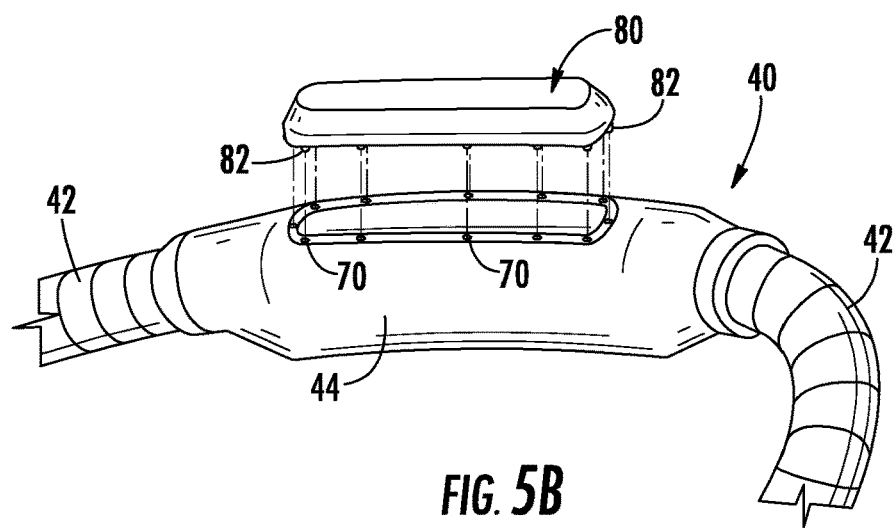
FIG. 5B is an exploded perspective view a third embodiment of an applicator device for cannulation of the arteriovenous graft including a cannulation chamber as shown in FIG. 5A.

In an alternative arrangement, a third embodiment of a fit-on applicator device is shown in FIG. 5B and generally designated at 80. In this embodiment, magnets 82 are provided on an inner peripheral surface of the applicator device 80 for aligning with the magnets 70 on the rim 46 of the cannulation chamber 44. It is understood that the applicator device and subcutaneous graft may include other means for interaction which are in addition, or as an alternative, to the magnets. Such interaction means may include sensors on the applicator device, the AVG or both. The sensors may interact to signal alignment, or a wand may be used as described above. The applicator device may include a light for the signal. The subcutaneous cannulation chambers may also glow under certain wavelengths, such as infrared. The interaction may also be mechanical, such as an audible click when the application device and cannulation chamber connect.

Figure 6:
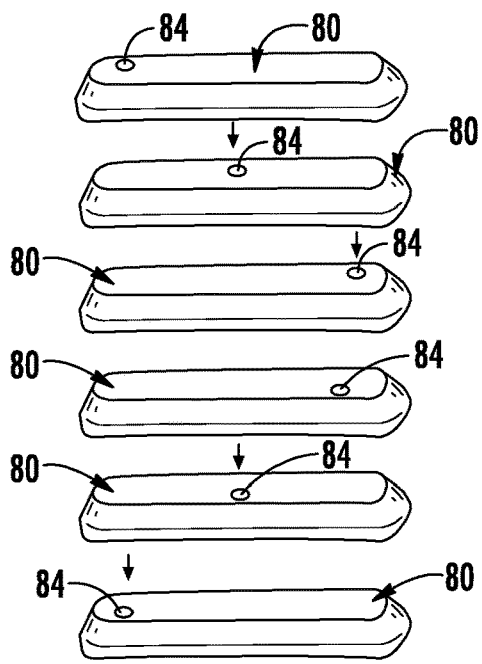
FIG. 6 is a perspective view of a plurality of applicator devices having sequentially spaced needle passages therethrough.
Figure 7:
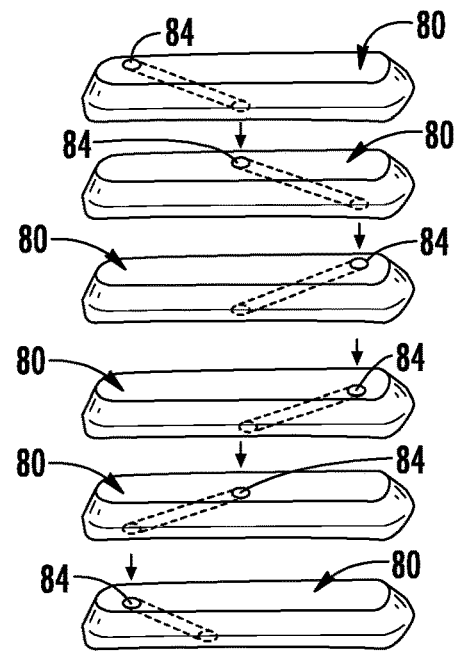
FIG. 7 is a perspective view of a plurality of applicator devices as shown in FIG. 6 wherein the needle passages are angled diagonally through the applicator devices.
Figure 8A:
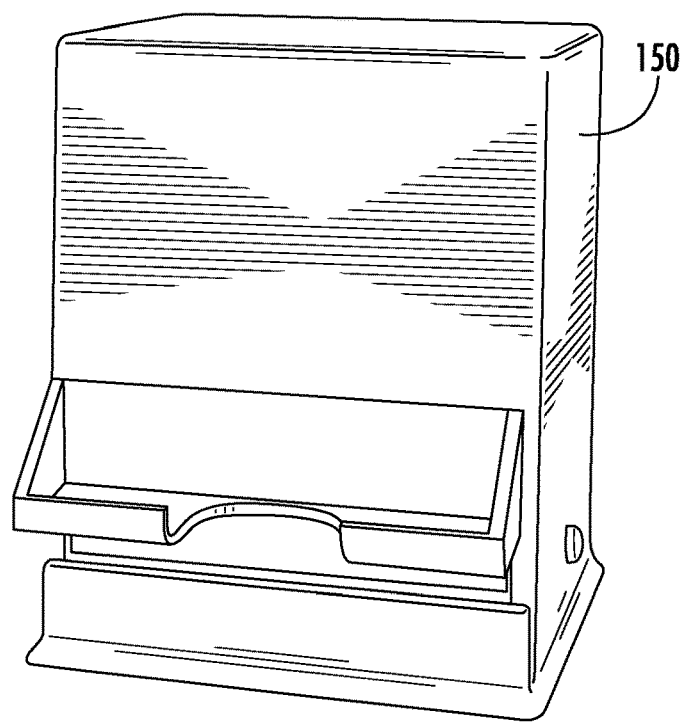
FIGS. 8A and 8B are perspective views of a dispensing cartridge for packaged applicator devices.
Figure 8B:
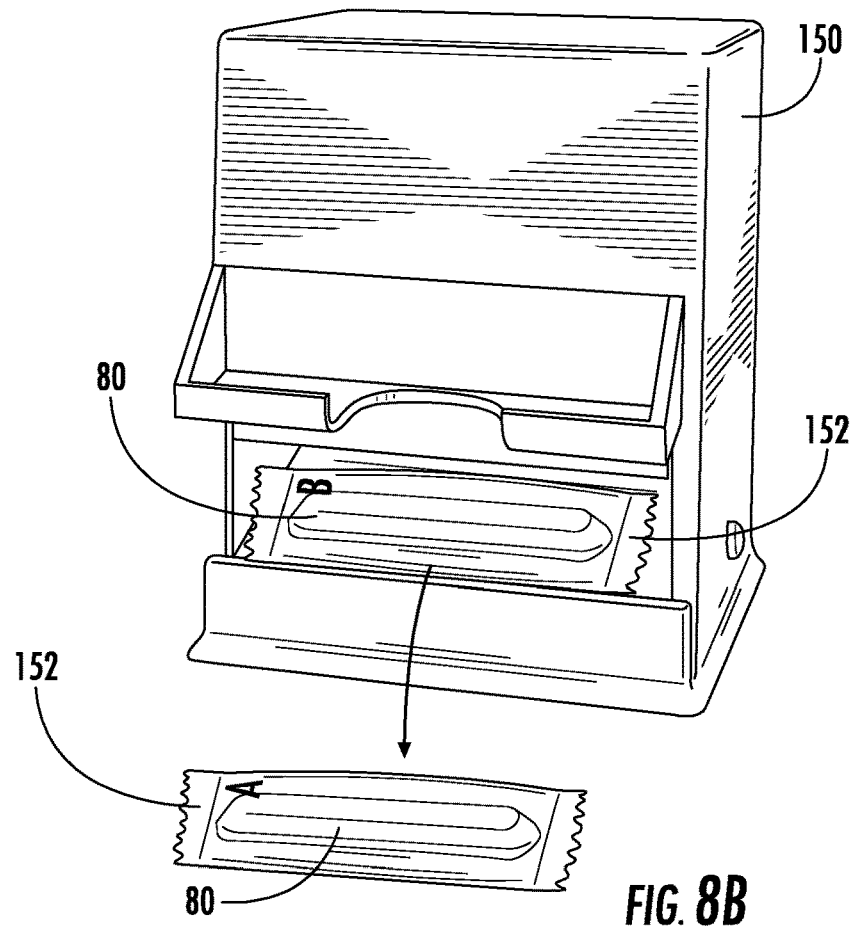

Referring now to FIG. 6, a plurality of the applicator devices 80 is shown. Each applicator device 80 has a needle passage 84 formed in a different position through the applicator device 80. According to the present apparatus and method, the user will use each applicator device 80 in sequence, one for each hemodialysis treatment. The needle passages 84 are in different positions to ensure that the user inserts the needle in a different location around the cannulation chamber 44. As shown in FIG. 7, the needle passages 84 may extend at angle rather than orthogonal to the surface of the applicator device 80. In this arrangement, the needle penetrates the port 47 in a manner so as to minimize damage to the material of the port 47. FIGS. 8A and 8B show an embodiment of a dispenser for the applicator devices. The dispenser preferably holds the applicator devices in a sequence which provides for appropriate spacing of needle passages to allow distribution around the cannulation site, which promotes healing between needle sticks and prolongs the life of the graft.

Figure 9:
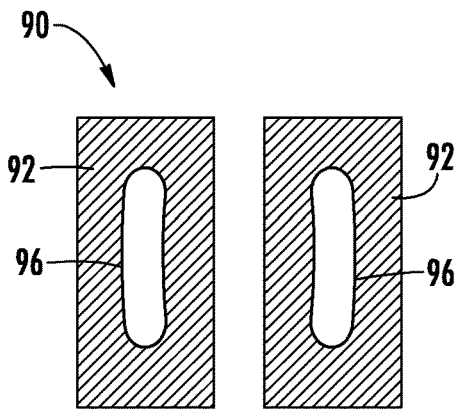
FIG. 9 is a top plan view of an embodiment of a pair of adhesive applicator devices for guiding cannulation of an arteriovenous graft including a pair of cannulation chambers.
Figure 10:
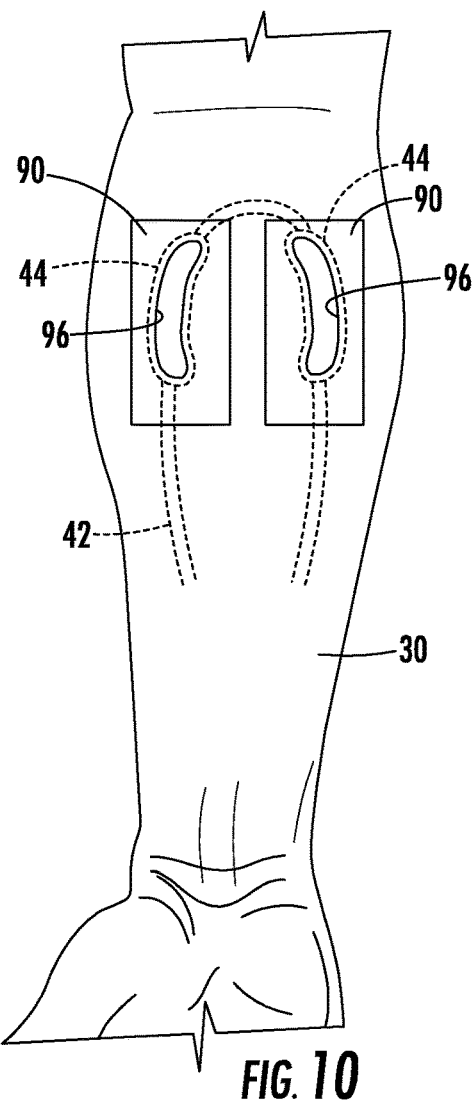
FIG. 10 is a top plan view of the pair of adhesive applicator devices as shown in FIG. 9 in position on an arm including a subcutaneous arteriovenous graft including a pair of cannulation chambers.
Figure 11A:
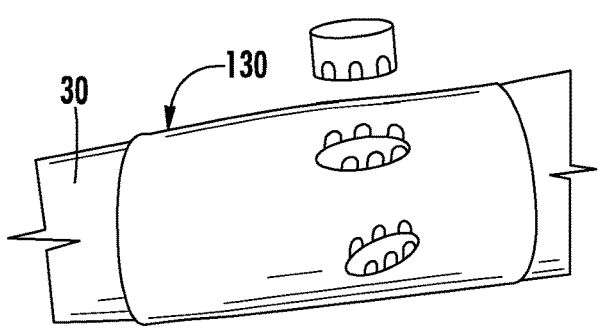
FIGS. 11A and 11B are perspective views of a fourth embodiment of an applicator device and a sleeve for cannulation of an arteriovenous graft.
Figure 11B:
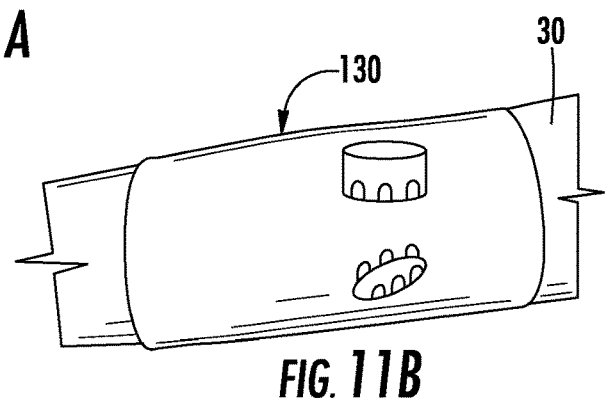

In another embodiment, the applicator device comprises a sheet, or sticker, as shown in FIGS. 9 and 10 and generally designated at 90. The sticker 90 is a thin, generally rectangular element comprising a planar upper surface 92, a lower surface 94 and an adhesive applied on the lower surface of the sticker. The sticker 90 may be releasably adhered to the surface of the skin 30 for indicating a location for cannulation of a vascular access graft 40. The sticker 90 defines a centrally disposed opening 96. The opening 96 as shown in FIG. 9 has a generally elongated ovular shape. Although the shape of the opening 96 is not critical, in practice the opening 96 should correspond to a feature of the AVG for alignment of the sticker 90 and the AVG. In the embodiment shown, the shape of the opening 96 in the sticker 90 corresponds to the size and shape of the cannulation chamber 44. The sticker 90 may comprise a soft, flexible material which allows the sticker to conform to any curvature of the surface of the skin 30 and the AVG 40 under the skin. Thus, the curvature of the skin and any bumps under the skin may vary without affecting the use of the sticker.

The bottom surface 94 of the sticker includes a layer of adhesive material for removably adhering the sticker to the skin 30 over the vascular access graft 40. Many types of adhesive are suitable for use with the sticker 90 as long as the adhesive allows firm bonding of the sticker 90 to the skin. The adhesive should also allow easy removal of the sticker 90 following use. The adhesive is preferably a pressure sensitive adhesive applied to the bottom surface 94 of the sticker 90. A wide variety of such adhesives are commercially available. In one embodiment, a portion of the edge of the bottom surface 94 of the sticker 90 may be devoid of adhesive to prevent that portion of the sticker from adhering to the skin 30. This configuration provides a location for a user to grasp the sticker 90 for removing the sticker from the skin 30. The adhesive material preferably does not leave any residue on the skin 30 when removed.

The sticker 90 may be any size sufficient to accommodate the cannulation chamber 44 of the vascular access graft 40, as well as providing an adhesive coated area large enough to provide a firm bond between the sticker 90 and the skin 30. In one embodiment, the sticker 90 may have an outer perimeter larger than the outer perimeter of the cannulation chamber 44 so as to fully surround the chamber when the sticker 90 is placed over the vascular access graft 40. As an alternative, only an edge region of the bottom surface 94 of the sticker 90 may be coated with the adhesive material.

The sticker 90 may further comprise a protective backing removably adhered to the bottom surface 94 of the sticker 90 over the adhesive layer. The removable protective backing prevents adhesion of the sticker 90 to undesired surfaces prior to use. Protective backings are well known in the art and typically comprise a variety of materials, such as paper treated with a release agent such as silicone, or alternatively a conformable material, for example, polyethylene, polyvinyl chloride, and the like. The removable protective backing may be the same size and shape as the sticker 90 or may be larger. In the embodiment described above, wherein the sticker 90 has a portion of the edge without adhesive, the user may grasp that portion for easily removing the backing from the sticker 90.

In use, the protective backing is manually removed from bottom surface 94 of the sticker 90 for exposing the adhesive. The sticker 90 is then ready to be affixed to the skin 30. The sticker 90 is positioned on the skin over the AVG 40 so that the opening 96 substantially surrounds the cannulation chamber 44. Once positioned, pressure is applied so that the sticker 90 is adhesively conformed to the skin 30. Once secured to the skin 30 around the cannulation chamber 44 of the vascular access graft 40, the sticker 90 will enable the user to determine a location for needle insertion. The sticker 90 thus provides an effective way of providing a means for indicating the cannulation location of an AVG.

In another embodiment, shown in FIGS. 13 and 14, the sticker 90 may be adapted to come apart upon removal from the skin 30. For example, a portion of the sticker 90 may be comprised of a material having low tear propagation resistance. In combination with a relatively strongly adhering adhesive on this portion of sticker, the sticker comes part when removed from a surface. More specifically, with removal of the sticker 90 from the skin 30, part of the material comprising the sticker 90 will remain on the skin. The portion of the sticker left behind on the skin is an indicia, such as a tick mark 98, is readily apparent to the human eye and indicates a point for needle insertion of the underlying AVG 40. A subsequent sticker 90 leaves a tick mark 98 on the skin 30 at the next site for cannulation. In another embodiment, shown in FIG. 14, when the sticker is removed boundary marks may remain on the skin, thereby providing an indication of position of the cannulation chamber. A suitable sticker according to this embodiment is shown in U.S. Pat. No. 4,268,983, the contents of which are hereby incorporated by reference, which describes an adhesive label comprising a support sheet and a fragile, easily tearable film adhered to the support sheet. If the label according to the '983 patent is removed from an article to which it has been applied, a portion of the fragile film comprising the label will tear and remain adhered to the substrate. U.S. Pat. No. 5,358,281, the contents of which are hereby incorporated by reference, describes an adhesive label which leaves components of the label on the surface, including visible indicia, when removed. It is understood that the indicia left behind on the skin surface may be alphanumeric characters which spell out words. U.S. Pat. No. 4,121,003, the contents of which are hereby incorporated by reference, also describes the transfer of alphanumeric characters upon removal of a label, wherein the characters comprise a material of low cohesion which, when the adhesive label is detached from a surface, the label splits within itself and remains in part on the surface to which it is adhered.

Figure 12:
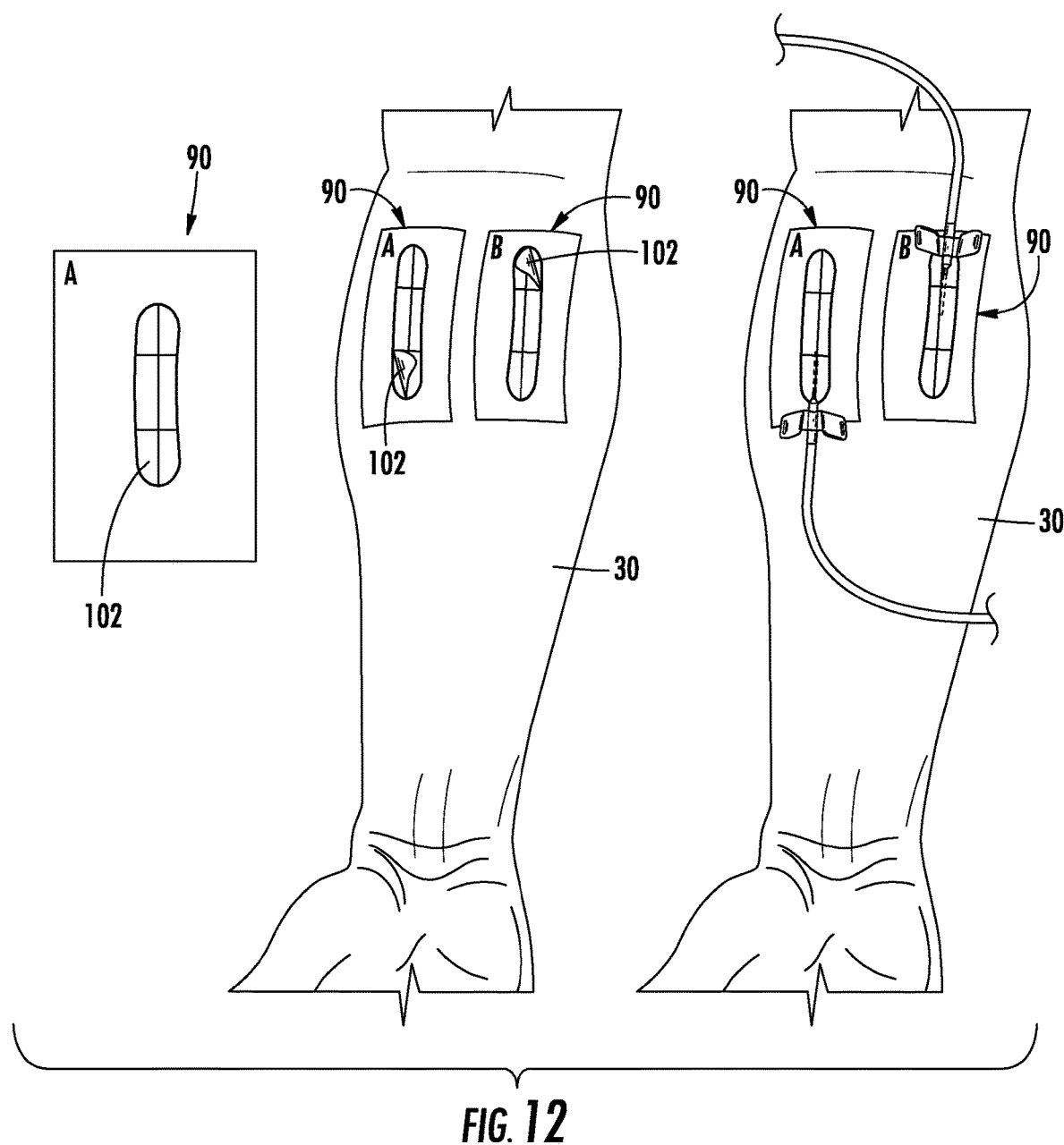
FIG. 12 is top plan views of an embodiment of an adhesive applicator device for guiding cannulation of a subcutaneous arteriovenous graft including each of a pair of cannulation chambers (not shown) for effecting hemodialysis.

In another embodiment as shown in FIG. 12, the sticker 90 is unitary with no openings. A portion of the sticker 90 configured to indicate the cannulation chamber 44 comprises sections for identifying potential sites for cannulation. One section 102 of the sticker 90 is removable. In use, the sticker 90 is applied to the skin 30 over the AVG 40. The section 102 of the sticker over the cannulation site is peeled from the skin 30 surface. The exposed skin 30 is then used as the site for needle insertion. U.S. Pat. No. 5,633,058, the contents of which are hereby incorporated by reference, describes a transparent printed indicia anchored weakly to a backing film which is stickered with a full area colored layer which anchors well to the backing film and to the printed indicia. The colored layer is coated with a self-adhesive composition.

Figure 15A:
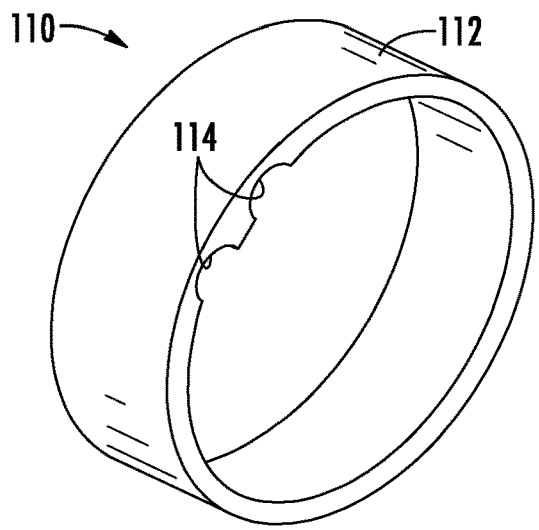
FIGS. 15A and 15B are perspective and elevation views of a flexible strap for use in cannulation of a subcutaneous arteriovenous graft.
Figure 15B:
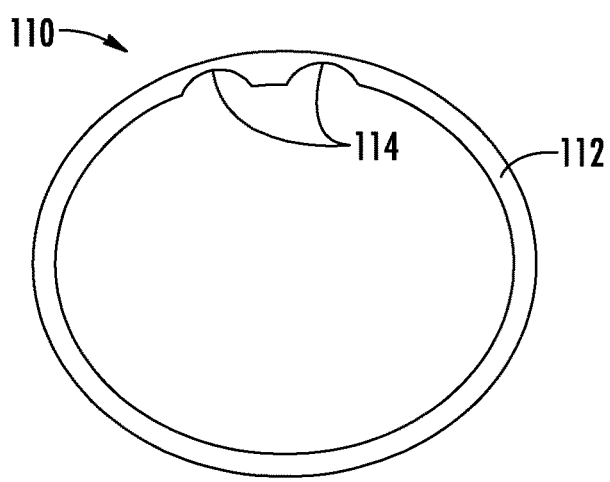
Figure 16:
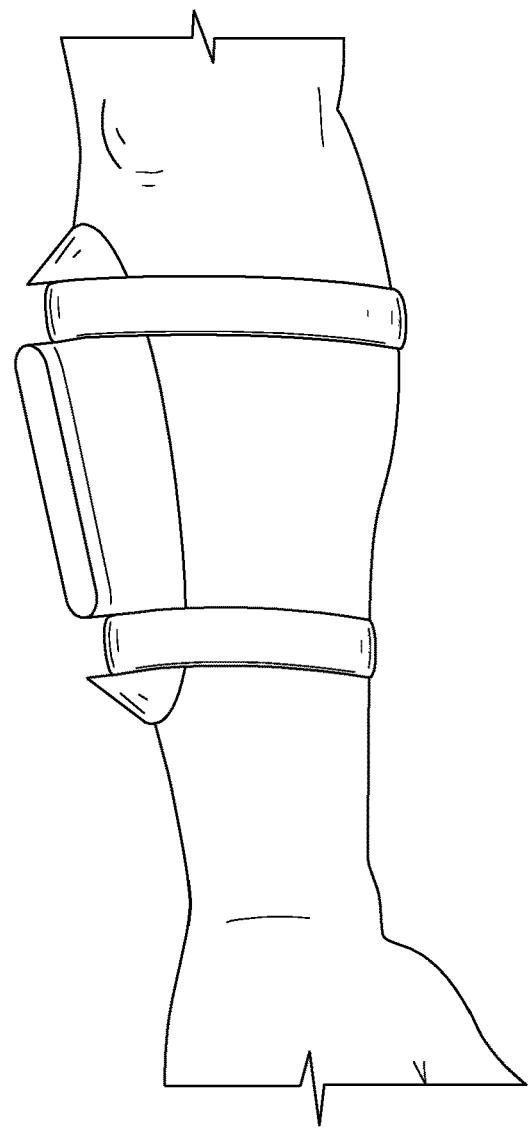
FIG. 16 is a top plan view of a pair of straps as shown in FIGS. 15A and 15B in place on an applicator device on an arm for guiding cannulation of a subcutaneous arteriovenous graft (not shown).

An embodiment for use in combination with an applicator device for positioning the applicator device for locating a point of cannulation of an implanted AVG is shown in FIGS. 15A and 15B and generally designated at 110. The combination comprises a pair of circular flexible straps 112 for securing the applicator device 116 to a body part of a user, which is an arm as shown in FIG. 16. The applicator device 116 has grooves 114 at each end for receiving the straps 112. In use, the applicator device 116 is positioned over the cannulation chamber 44 as described above. The straps 112 then secure the applicator device in place for subsequent cannulation. One advantage of this arrangement is that following hemodialysis and removal of the needle, the straps 112 urge the applicator device 116 against the arm providing pressure to aid in stopping bleeding.

Figure 17:
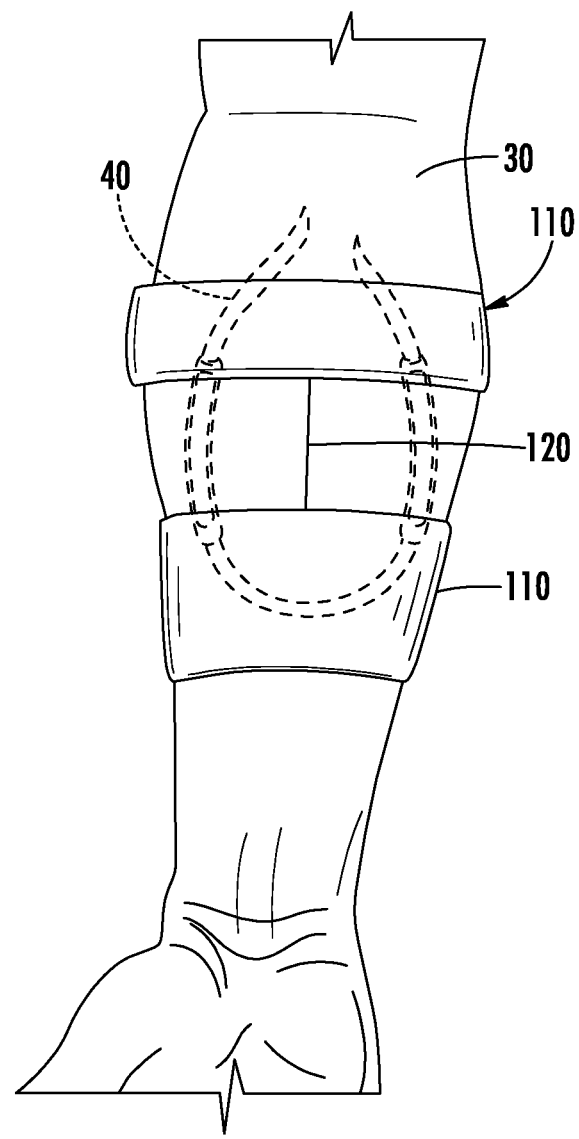
FIG. 17 is a top plan view of a pair of straps as shown in FIGS. 15A and 15B in place on an arm for guiding cannulation of a subcutaneous arteriovenous graft including each of a pair of cannulation chambers shown in phantom.

Another embodiment of an apparatus and method for guiding cannulation of an arteriovenous graft using straps 112 is shown in FIG. 17. In this embodiment, the straps 112 provide a means for locating the cannulation chambers 44 for subsequent cannulation. Each of the straps 112 has two circumferentially spaced notches 118 in an inner surface 120. The notches 118 are configured to receive the ends of a pair of cannulation chambers 44 when placed over an AVG 40 in the patient. Together the straps 112 show the user the ends of the cannulation chambers 44 for aiding the user in identifying a location for cannulation. The straps 112 serve to anchor the cannulation chambers 44 prevent any movement of the device. In this manner, the device may be fixed to a cannulation chamber on either end.

Figure 18:
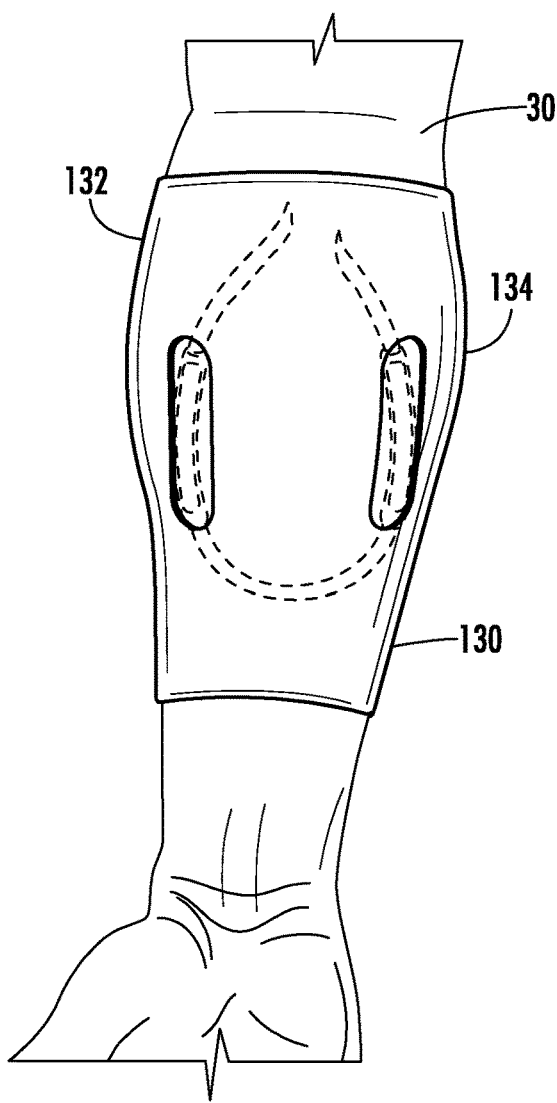
FIG. 18 is a top plan view of an embodiment of a sleeve in place on an arm for guiding cannulation of a subcutaneous arteriovenous graft including each of a pair of cannulation chambers shown in phantom.

Referring now to FIG. 18, still another embodiment of an applicator device for determining a location for cannulation of a vascular access graft 40 is shown and generally designated at 130. In this embodiment, the applicator device 130 is a sleeve 132 for sliding over the arm. The sleeve 132 is made of a flexible, resilient fabric so that the sleeve 132 stays tightly on the arm when worn. The sleeve 132 defines a pair of circumferentially spaced openings 134 having a generally elongated ovular shape. Although the shape of the openings 134 is not critical, in practice the openings 134 should correspond to the shape of the AVG or a feature of the AVG for alignment of the openings and the AVG. In the embodiment shown, the shape of the openings 134 in the sleeve 132 corresponds to the size and shape of the cannulation chambers 44.

Figure 19:
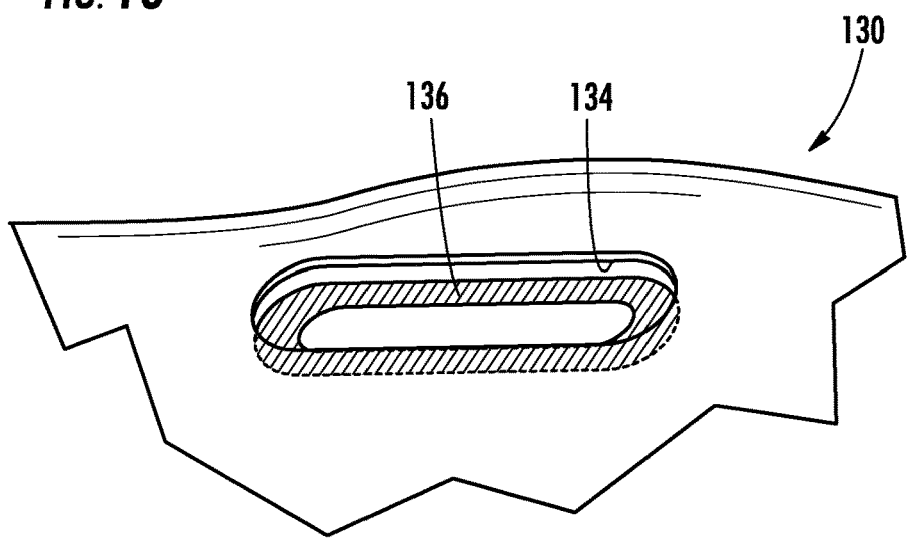
FIG. 19 is an up close perspective view of the sleeve as shown in FIG. 18 showing a pocket for receiving an applicator device for guiding cannulation of a subcutaneous arteriovenous graft.

In use, the sleeve 132 is positioned on the arm with the openings over the cannulation chambers 44. The user can then cannulate the vascular access graft 40. In a further embodiment, each of the openings 134 in the sleeve 132 forms a pocket 136 with a layer of material adjacent the skin 30 (FIG. 19). The pockets 136 are configured to receive an applicator device for use in locating and cannulating the AVG (FIG. 20).

The apparatus and method for cannulation of a vascular access graft as described herein has many advantages, including providing a reliable means for allowing a user to perform hemodialysis while consistently and accurately accessing an implanted graft site. Using an external device to identify and localize the position of the implanted device reduces incorrect cannulations, and facilitates increased patency of the vascular access graft after surgical implantation into the body. Fewer missed needle insertions and cannulation errors reduce opportunity for damaging, destroying, or displacing the implanted graft due to incorrect insertion of the cannula or improper or repeated needle sticks attempting to "hit" the proper insertion site on the subcutaneous graft. Cumulative damage inflicted by repetitive needle puncture weakens the graft wall and creates conditions for pseudoaneurysm formation. An AVG sustains roughly 300 needle sticks a year. The apparatus and method as described herein providing for needle rotation to evenly distribute the needle damage over the entire length of the graft helps minimize or delay pseudoaneurysm formation.

The present apparatus tracks the location of cannulation sites to therefore be assured that proper needle rotation is taking place. A system or sequence designed to facilitate needle rotation facilitates proper needle rotation throughout a cannulation site area by maintaining compliance with the facilitated cannulation sequence.

The invention also enhances the ability of a patient or medical personnel to properly and accurately identify the placement of the implanted vascular access grafts to ensure proper placement. The vascular access graft may be visualized by conventional medical imaging means, including, for example, x-ray, magnetic resonance imaging, and/or computer-aided tomography (CT).

Although the present invention has been shown and described in considerable detail with respect to only a few exemplary embodiments thereof, it should be understood by those skilled in the art that I do not intend to limit the invention to the embodiments since various modifications, omissions and additions may be made to the disclosed embodiments without materially departing from the novel teachings and advantages of the invention, particularly in light of the foregoing teachings. For example, the present invention is suitable for use in a number of vascular access devices and applications. Accordingly, we intend to sticker all such modifications, omission, additions and equivalents as may be included within the spirit and scope of the invention as defined by the following claims. In the claims, means-plus-function clauses are intended to sticker the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. A guiding apparatus for guiding cannulation with a dialysis needle of an arteriovenous dialysis access graft subcutaneously implanted in a body of a subject, the arteriovenous dialysis graft including a flexible conduit defining a longitudinal flow passageway and having a first end portion configured to connect to a first blood vessel of the subject and a second end portion configured to connect to a second blood vessel of the subject such that blood flows through the longitudinal flow passageway of the flexible conduit from the first end portion to the second end portion, and a cannulation chamber defining a cannulation port, the flexible conduit extending through the cannulation chamber for receiving the needle inserted through the cannulation port, the guiding apparatus comprising:
an elongated body member having a first end, a second end, a longitudinal axis extending between the first end and the second end, and an inner surface, the body member comprising
a planar base portion terminating in longitudinal edges substantially parallel to the longitudinal axis of the body member, a distance between the longitudinal edges of the base portion being substantially equal to a lateral dimension of the cannulation chamber, and
legs extending from the longitudinal edges of the base portion in a direction transverse to the the base portion, the legs terminating in longitudinal edges, the base portion and legs defining an open longitudinal channel for receiving the cannulation chamber,
wherein the body member is adapted to be secured adjacent the cannulation chamber such that the legs operatively engage the cannulation chamber for aligning the inner surface of the base portion with the cannulation port for guiding location of a needle insertion through the body member and into the cannulation chamber.

2. The guiding apparatus as recited in claim 1, wherein the body member is adapted to extend from a first end to a second end of the cannulation chamber.

3. The guiding apparatus as recited in claim 1, wherein the body member has at least one passage opening into the inner surface of the body member for passing the dialysis needle.

4. The guiding apparatus as recited in claim 3, wherein the at least one passage is orthogonal to the inner surface of the body member.

5. The guiding apparatus as recited in claim 3, wherein the at least one passage extends at an angle greater than or less than 90 degrees with respect to the inner surface of the body member.

6. A guiding apparatus for guiding cannulation with a dialysis needle of an arteriovenous dialysis access graft subcutaneously implanted in a body of a subject, the arteriovenous dialysis graft including a flexible conduit defining a longitudinal flow passageway and having a first end portion configured to connect to a first blood vessel of the subject and a second end portion configured to connect to a second blood vessel of the subject such that blood flows through the longitudinal flow passageway of the conduit from the first end portion to the second end portion, and a cannulation chamber defining a cannulation port, the conduit extending through the cannulation chamber for receiving the needle inserted through the cannulation port, the guiding apparatus comprising:
an elongated body member having a first end, a second end, a longitudinal axis extending between the first end and the second end, and an inner surface, the body member comprising
a planar base portion terminating in longitudinal edges substantially parallel to the longitudinal axis of the body member, a distance between the longitudinal edges of the base portion being substantially equal to a lateral dimension of the cannulation chamber, and
a sidewall depending transversely from the longitudinal edges of the base portion, the sidewall defining longitudinally spaced notches,
wherein the body member is adapted to be secured adjacent the subcutaneous cannulation chamber such that the notches operatively receive the cannulation chamber for aligning the inner surface of the base portion with the cannulation port for guiding location of a needle insertion through the body member and into the cannulation chamber.

7. The guiding apparatus as recited in claim 6, wherein the body member is adapted to extend from a first end to a second end of the cannulation chamber.

8. The guiding apparatus as recited in claim 6, wherein the body member has at least one passage opening into the inner surface of the body member for passing the needle.

9. The guiding apparatus as recited in claim 8, wherein the at least one passage is orthogonal to the inner surface of the body member.

10. The guiding apparatus as recited in claim 8, wherein the at least one passage extends at an angle greater than or less than 90 degrees with respect to the inner surface of the body member.

* * * * *